US008834657B2

(12) United States Patent
Claude et al.

(10) Patent No.: US 8,834,657 B2
(45) Date of Patent: Sep. 16, 2014

(54) METHOD OF MANUFACTURING AN MRI COMPATIBLE CONDUCTIVE LEAD BODY

(75) Inventors: Timothy J. Claude, Coon Rapids, MN (US); Lois Claude, legal representative, Coon Rapids, MN (US); Cherik T. Bulkes, Sussex, WI (US); Mary K. Norby, Menomonee Falls, WI (US)

(73) Assignee: Kenergy, Inc., Mequon, WI (US)

( * ) Notice: Subject to any disclaimer, the term of this patent is extended or adjusted under 35 U.S.C. 154(b) by 470 days.

(21) Appl. No.: 13/199,097

(22) Filed: Aug. 19, 2011

(65) Prior Publication Data

US 2012/0043011 A1  Feb. 23, 2012

Related U.S. Application Data

(60) Provisional application No. 61/401,867, filed on Aug. 20, 2010.

(51) Int. Cl.
*B32B 38/10* (2006.01)
*B29D 23/00* (2006.01)
*B29C 61/00* (2006.01)
*A61N 1/08* (2006.01)
*B29L 31/00* (2006.01)
*B29C 53/32* (2006.01)

(52) U.S. Cl.
CPC ............ *B29D 23/001* (2013.01); *B29C 61/006* (2013.01); *A61N 2001/086* (2013.01); *B29L 2031/753* (2013.01); *B29C 53/32* (2013.01)
USPC ...................................................... 156/172

(58) Field of Classification Search
CPC .......................... A61N 2001/086; B29C 53/32

USPC ........................................................... 156/173
See application file for complete search history.

(56) References Cited

U.S. PATENT DOCUMENTS

| 2,966,640 | A | 12/1960 | Eiland, Jr. |
| 5,217,010 | A | 6/1993 | Tsitlik et al. |
| 5,861,019 | A | 1/1999 | Sun et al. |
| 6,009,350 | A | 12/1999 | Renken |
| 6,324,431 | B1 | 11/2001 | Zarinetchi et al. |
| 6,713,671 | B1 | 3/2004 | Wang |
| 6,930,242 | B1 | 8/2005 | Helfer |
| 7,112,298 | B2 * | 9/2006 | Kampa et al. ............... 264/301 |
| 7,363,090 | B2 | 4/2008 | Halperin et al. |
| 7,917,213 | B2 | 3/2011 | Bulkes et al. |

(Continued)

FOREIGN PATENT DOCUMENTS

| EP | 1704893 A1 | 9/2006 |
| WO | 2005110540 A1 | 11/2005 |

(Continued)

*Primary Examiner* — Michael Orlando
*Assistant Examiner* — Marta Dulko
(74) *Attorney, Agent, or Firm* — Quarles & Brady LLP; George E. Haas

(57) ABSTRACT

A method of manufacturing an implantable electrical lead body MRI used in such applications as cardiac pacing, electrical nerve stimulation and intracardiac defibrillation applications that is biocompatible upon implantation in an animal and compatible with a magnetic resonance imaging scanner for the purpose of diagnostic quality imaging is disclosed. The method involves a relatively rigid first substrate layer, a conductive coil layer being precisely placed over the first substrate layer, a relatively soft second substrate layer over the conductive coil layer and a relatively rigid third substrate layer over the second substrate layer.

23 Claims, 7 Drawing Sheets

(56) References Cited

U.S. PATENT DOCUMENTS

| | | |
|---|---|---|
| 8,170,687 B2 * | 5/2012 | Min et al. .................. 607/116 |
| 2002/0123776 A1 | 9/2002 | Von Arx et al. |
| 2003/0036776 A1 | 2/2003 | Foster |
| 2003/0050557 A1 | 3/2003 | Susil et al. |
| 2003/0144721 A1 | 7/2003 | Villaseca et al. |
| 2004/0230271 A1 | 11/2004 | Wang et al. |
| 2006/0212096 A1 | 9/2006 | Stevenson |
| 2006/0217792 A1 | 9/2006 | Hussein et al. |
| 2006/0247684 A1 | 11/2006 | Halperin et al. |
| 2007/0112398 A1 | 5/2007 | Stevenson et al. |
| 2008/0033497 A1 * | 2/2008 | Bulkes et al. .................. 607/9 |
| 2008/0033500 A1 | 2/2008 | Strother et al. |
| 2008/0243218 A1 * | 10/2008 | Bottomley et al. .......... 607/116 |
| 2009/0281592 A1 | 11/2009 | Vase |
| 2010/0049290 A1 * | 2/2010 | Min et al. .................. 607/127 |
| 2010/0331942 A1 * | 12/2010 | Cholette et al. .............. 607/127 |
| 2012/0043011 A1 * | 2/2012 | Claude et al. ................ 156/172 |

FOREIGN PATENT DOCUMENTS

| | | |
|---|---|---|
| WO | 2006023700 A | 3/2006 |
| WO | 2006093685 A | 9/2006 |
| WO | 2006105066 A | 10/2006 |

* cited by examiner

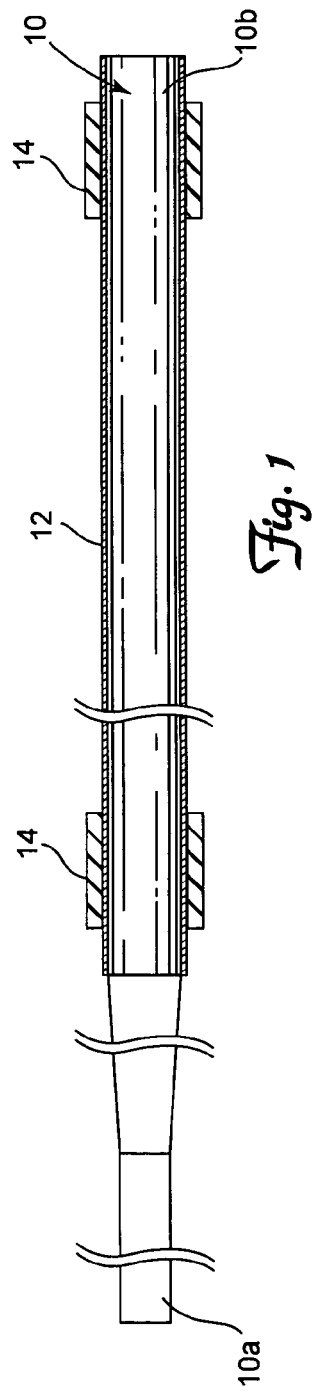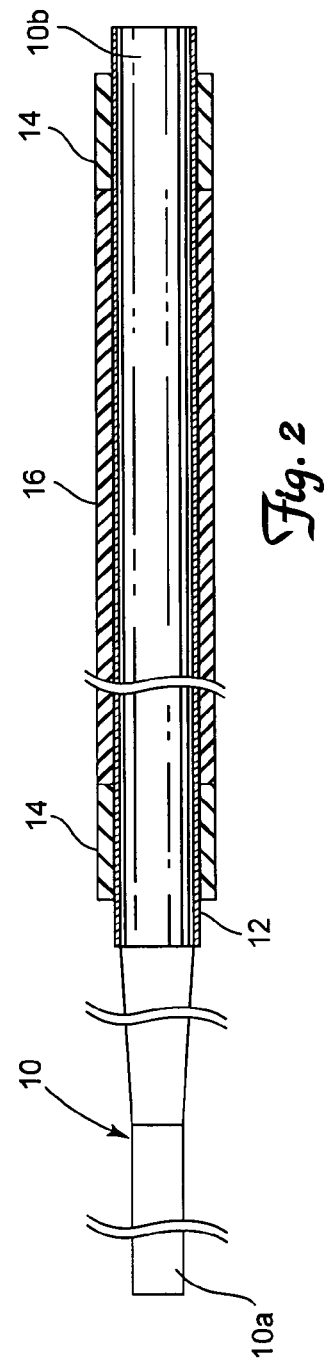

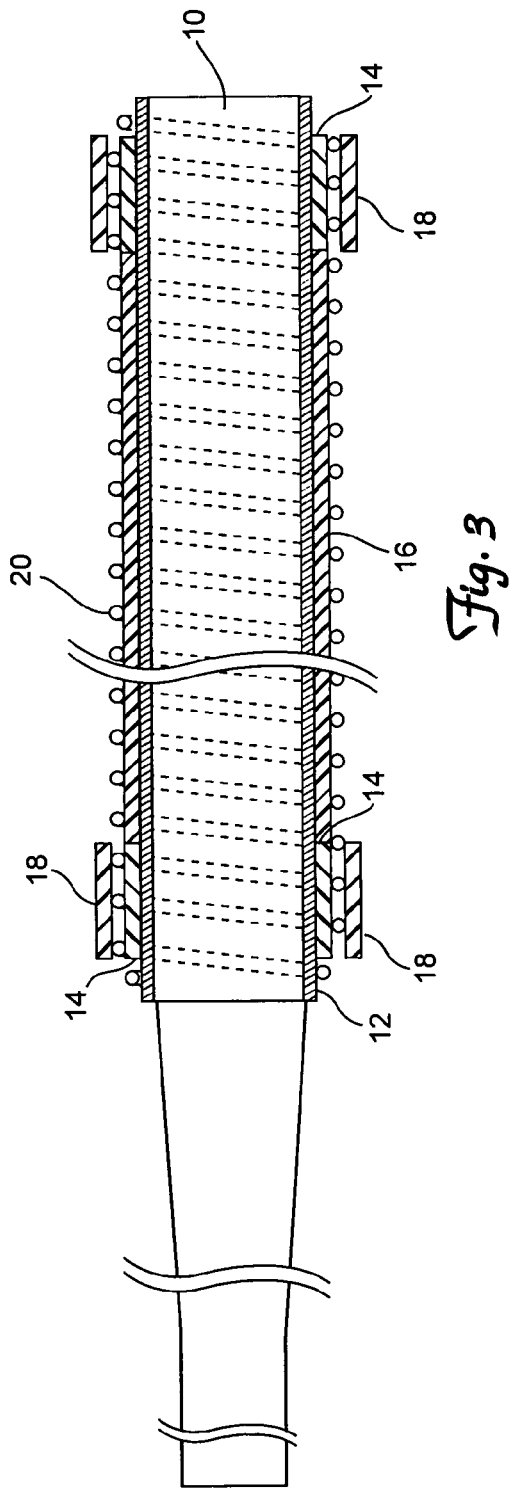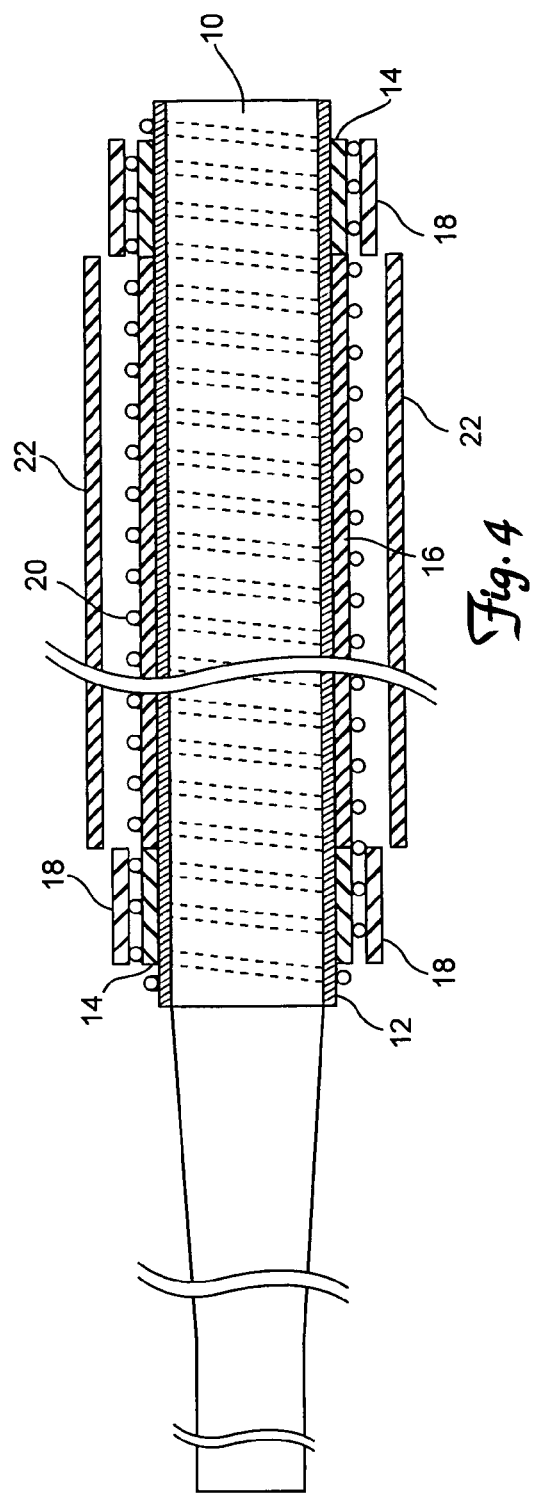

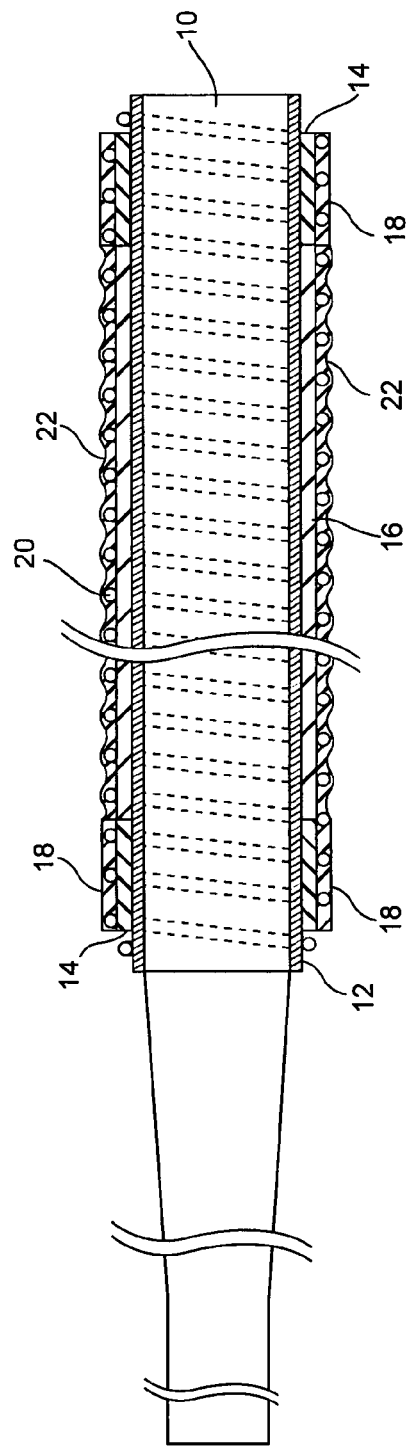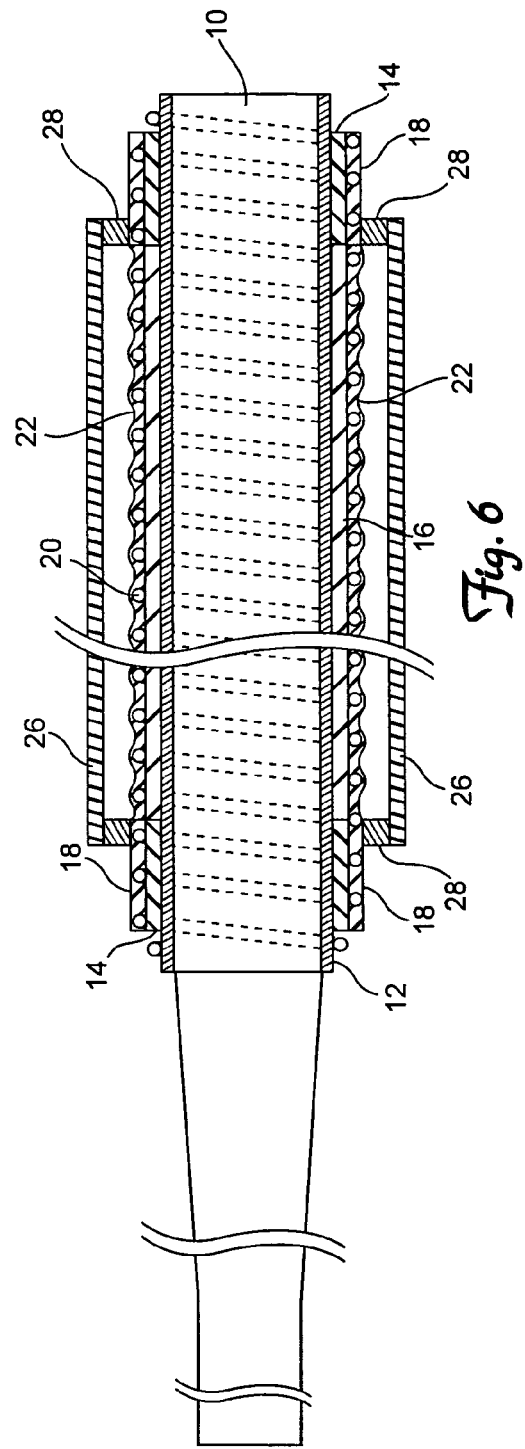

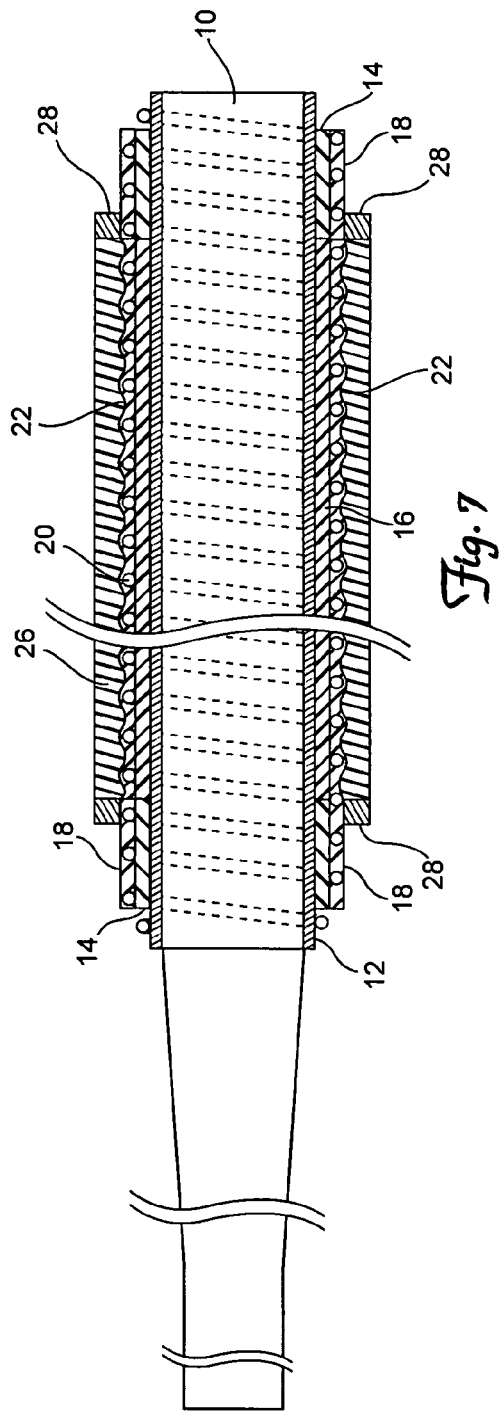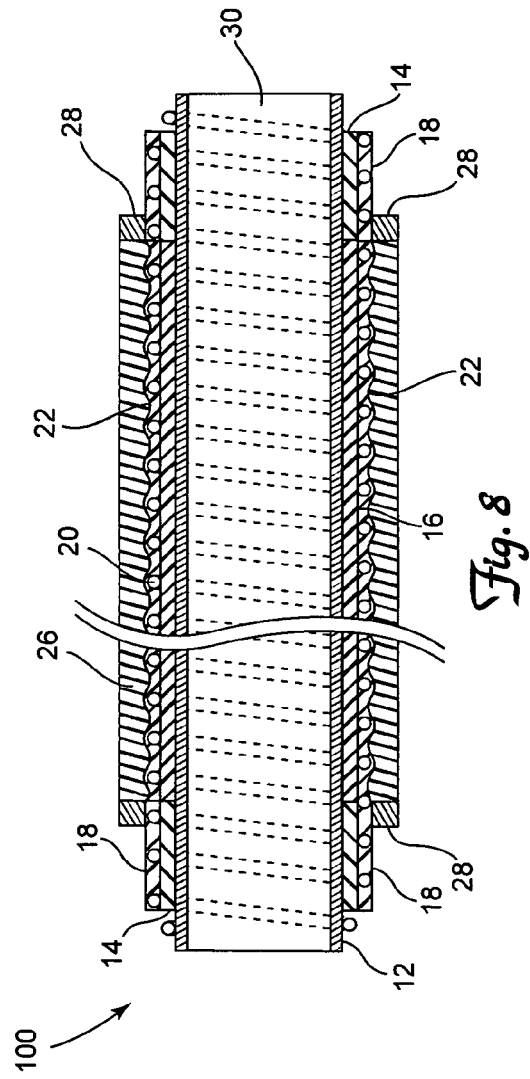

METHOD OF MANUFACTURING AN MRI COMPATIBLE CONDUCTIVE LEAD BODY

FIELD OF THE INVENTION

The invention relates to methods of manufacturing an implantable electrically conductive lead body used in such applications as cardiac pacing, intracardiac defibrillation and electrical nerve stimulation that is biocompatible upon implantation in an animal and compatible with a magnetic resonance imaging scanner for the purpose of diagnostic quality imaging.

BACKGROUND

Magnetic Resonance Imaging (MRI) is commonly used to view the internal organs of medical patients. To create an image, the patient is placed into very strong static and varying magnetic and radio frequency (RF) fields. For this reason, MRI is generally prohibited for patients with implanted ferromagnetic and/or electrically conductive objects, such as pacemakers, implantable defibrillators and nerve stimulators. Although it is feasible to minimize and even eliminate the use of ferromagnetic materials in implanted devices, these types of devices still require electrically conductive components that are affected by the fields produced by an MRI scanner.

U.S. Pat. No. 7,917,213, authored by the inventors of the present invention and incorporated herein by reference describes in detail the electrical and dimensional parameters of an MRI compatible lead body which minimizes the induced voltages and currents that can cause localized heating and/or distortion of an MRI image. This design requires that the diameter and pitch of the conductive coil within the lead body be closely controlled over its entire length.

Current methods of producing implantable lead bodies utilize various methods of polymer deposition such as spraying, dip coating, and extruding, however, these methods do not provide axial and diametric control of the conductive coil within the required tolerances and are thus unsuitable for producing MRI compatible lead bodies.

The invention as described and claimed herein details a process for manufacturing MRI compatible lead bodies which maintains close control of the helix pitch as well as the position of the coil in relation to the center line of the lead body, both of which relate to achieving the target RF performance.

SUMMARY

In one embodiment the invention discloses a method of manufacturing an MRI compatible conductive lead body. The method includes providing a mandrel defining a first end, a second end and an outer diameter and then applying a first substrate layer over the mandrel, with the first substrate layer defining an outer surface. The first substrate layer is next reflowed to conform closely to the mandrel. A conductive coil layer is wound around the outer surface of the first substrate layer and then secured to the mandrel at least at the first end and the second end. A second substrate layer is applied over the outer surface of the first substrate layer and reflowed to fuse with the first substrate layer and the conductive coil layer, permanently securing the conductive coil layer to the lead body. A third substrate layer is applied over the outer surface of the second substrate layer and reflowed causing the third substrate layer to fuse with the second substrate layer. The lead body is removed from the mandrel and trimmed to expose the conductive coil layer, allowing the lead body to be capable of electrical communication.

In another embodiment the invention discloses a method of manufacturing an MRI compatible conductive lead body. The method includes providing a mandrel defining a first end and a second end and an outer dimension substantially conforming to a desired inner dimension of a lumen defined by the lead body, with the mandrel coated with a non-stick material. A first set of blockers is placed at the first and second end of the mandrel, with the first set of blockers serving to prevent the migration of subsequently applied layers during the manufacturing process. A first substrate layer is applied between the first set of blockers, followed by the application of a first length of heat shrink material over the first substrate layer. The first length of heat shrink material is exposed to a sufficient amount of heat for a sufficient length of time to cause the first substrate layer to reflow, resulting in the first substrate layer conforming to the coated mandrel. Following reflowing of the first substrate layer, the first length of heat shrink material is removed. A conductive coil layer is wound over the outer surface of the first substrate layer and secured to the mandrel. A second set of blockers is placed at the first and second end of the lead body followed by applying a second substrate layer between the second set of blockers. A second length of heat shrink material is placed over the second substrate layer and exposed to a sufficient amount of heat for a sufficient length of time to cause the second substrate layer to reflow, resulting in the second substrate layer encapsulating the conductive coil layer and fusing with the first substrate layer. The second length of heat shrink material is removed and discarded. A third substrate material is placed over the second substrate layer. A third length of heat shrink material is applied over the third substrate and exposed to a sufficient amount of heat for a sufficient length of time to cause the third substrate layer to reflow and fuse to the second substrate layer. The third length of heat shrink material is removed and discarded. The first, second and third set of blockers are loosened from the mandrel, allowing the lead body to be removed from the mandrel. Upon removing the lead body from the mandrel the blockers are removed to expose the conductive coil layer, allowing the lead body to be capable of electrical communication.

BRIEF DESCRIPTION OF THE DRAWINGS

FIG. 1 is a longitudinal cross section of a non-stick coated mandrel with a first set of blockers attached.

FIG. 2 is a longitudinal cross section of the lead body shown in FIG. 1 with a first substrate applied following reflowing of the first substrate.

FIG. 3 is a longitudinal cross section of the lead body shown in FIG. 2 following the winding of a conductive coil layer and an attached second set of blockers.

FIG. 4 is a longitudinal cross section of the lead body shown in FIG. 3 following the application of a second substrate prior to reflowing the second substrate.

FIG. 5 is a longitudinal cross section of the lead body shown in FIG. 4 following reflowing the second substrate.

FIG. 6 is a longitudinal cross section of the lead body shown in FIG. 5 following the application of a third substrate prior to reflowing the third substrate.

FIG. 7 is a longitudinal cross section of the lead body following reflowing of the third substrate.

FIG. 8 is a longitudinal cross section of the lead body following removal of the mandrel.

DETAILED DESCRIPTION

Figure 9:
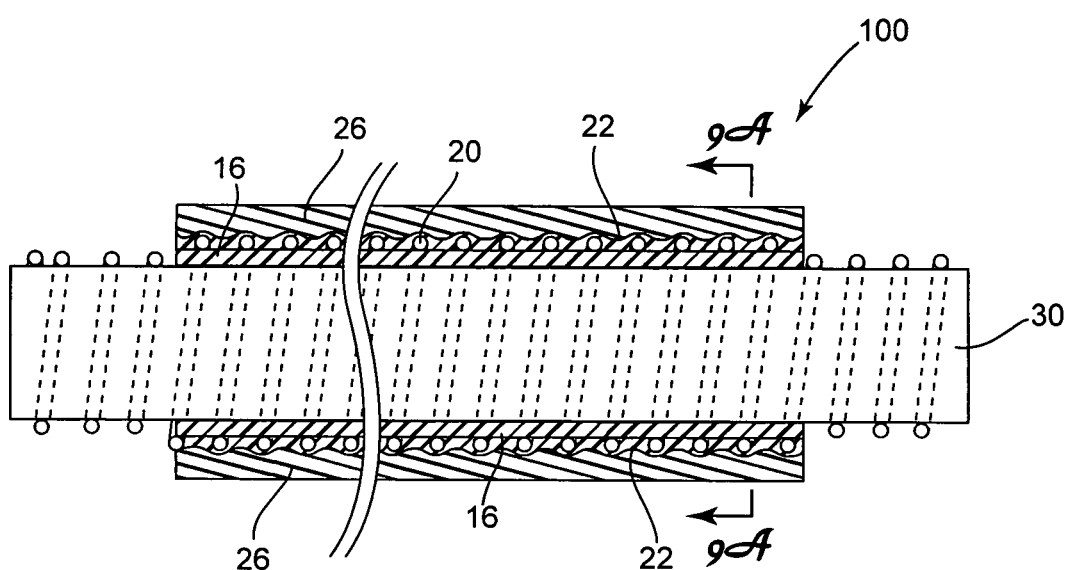
FIG. 9 is a longitudinal cross section of the completed lead body.

The particulars shown herein are by way of example and for purposes of illustrative discussion of the invention only and are presented in the cause of providing what is believed to be the most useful and readily understood description of the principles and conceptual aspects of the invention. In this regard, no attempt is made to show structural details of the invention in more detail than is necessary for the fundamental understanding of the invention, the description taken with the drawings making apparent to those skilled in the art how the several forms of the invention may be embodied in practice.

Nomenclature
10 Mandrel
10a Tapered End of Mandrel
10b Non-Tapered End of Mandrel
12 Coating
14 First Blocker
16 First Substrate Layer
18 Second Blocker
20 Conductive Coil Layer
22 Second Substrate Layer
26 Third Substrate Layer
28 Third Blocker
30 Lumen
50 Step of Providing Non-Stick Coated Mandrel
52 Step of Placing $1^{st}$ Set of Blockers on Mandrel
54 Step of Applying $1^{st}$ Substrate Between $1^{st}$ Set of Blockers
56 Step of Applying $1^{st}$ Length of Heat Shrink Material Over $1^{st}$ Substrate Layer
58 Step of Exposing $1^{st}$ Length of Heat Shrink Material to Sufficient Heat to Reflow $1^{st}$ Substrate Layer
60 Step of Removing $1^{st}$ Length of Heat Shrink Material
62 Step of Winding Conductive Coil Layer Over $1^{st}$ Substrate Layer
64 Step of Placing $2^{nd}$ Set of Blockers Over Conductive Coil Layer and $1^{st}$ Substrate Layer
66 Step of Applying $2^{nd}$ Substrate Layer Over Conductive Coil Layer Between $2^{nd}$ Set of Blockers
68 Step of Applying $2^{nd}$ Length of Heat Shrink Material Over $2^{nd}$ Substrate Layer
70 Step of Exposing $2^{nd}$ Length of Heat Shrink Material to Sufficient Heat to Reflow $2^{nd}$ Substrate Layer
72 Step of Removing $2^{nd}$ Length of Heat Shrink Material
74 Step of Applying $3^{rd}$ Set of Blockers
76 Step of Applying $3^{rd}$ Substrate Layer Over Reflowed $2^{nd}$ Substrate Layer, Between $3^{rd}$ Set of Blockers
78 Step of Applying $3^{rd}$ Length of Heat Shrink Material Over $3^{rd}$ Substrate Layer
80 Step of Exposing $3^{rd}$ Length of Heat Shrink Material to Sufficient Heat to Reflow $3^{rd}$ Substrate Layer
82 Step of Removing $3^{rd}$ Length of Heat Shrink Material
84 Step of Loosening $1^{st}$, $2^{nd}$ $3^{rd}$ Blockers from Mandrel
86 Step of Removing Lead Body from Mandrel
88 Step of Trimming Away Blockers to Expose the Conductive Winding Layer at Both Ends of Lead Body
100 Conductive Lead body Definitions "Filar" means the number of separate conductive strands wound onto the lead body.

"Reflow" means applying sufficient pressure and temperature to a polymeric material to cause it to change configuration.

"Teflon®" is used here in its generic sense and includes PTFE, ETFE, FEP and other non-stick coatings.

Construction

As best shown in FIG. 1, the method begins with step 50 the procurement of a mandrel 10, which can be stainless steel, Teflon® or other materials able to withstand the temperatures and pressures of the method of the present invention. The mandrel 10 defines an outer dimension which will eventually correspond to the inner dimension of the lumen 30 of the eventually completed lead body 100. The mandrel 10 also defines a tapered end 10a and a non-tapered end 10b. The tapered end 10a serves to facilitate easier loading of the first 16, second 22 and third 26 substrate layers onto the mandrel 10 as well as the heat shrink material (not shown) used to reflow the first 16, second 22 and third 26 substrate layers. In this embodiment, the mandrel 10 is coated with a layer of non-stick coating 12 such as Teflon® or another compound characterized by chemical inertness as well as possessing significant non-stick characteristics. In one embodiment, the mandrel comprises a stainless steel wire with a sheet of Teflon® applied to it. A first set of blockers 14 at step 52 is placed over the Teflon® coated 12 mandrel 10 and serves to assist in preventing the migration of subsequently applied layers during the manufacturing process. In one embodiment the first set of blockers 14 comprise a heat shrink material that is heated following application causing the blockers 14 to decrease in size and closely conform to the outer contours of the mandrel 10. The first set of blockers 14 can be made of PET (polyethylene terephthalate) heat shrink material, however, it is noted that other materials possessing similar characteristics would also work, thus the invention is not considered to be so limited.

FIG. 2 shows the lead body following step 54 and the application of a first substrate layer 16 between the first set of blockers 14 which serves to create a uniform outer diameter as well as acting to add structural strength to the eventually completed lead body 100. In one embodiment, the first substrate layer is made of a 55 D polyurethane material such as Pellethane, made by Dow Chemical, which is relatively rigid and adds strength and integrity to the eventually completed lead body 100. In other embodiments, the first substrate layer 16 can also be made of other urethane, silicone or other polymeric materials able to withstand the temperature and pressure requirements necessary to reflow and provide the necessary biocompatibility. The first substrate layer 16 is applied to the mandrel 10 as a tube which is slid over the tapered end 10a of mandrel 10 followed at step 56 by sliding a tube of a first length of heat shrink material (not shown) also over the tapered end 10a, over the not yet reflowed first substrate layer 16. The first length of heat shrink material (not shown) is then at step 58 exposed to heat for a period of time sufficient to cause the first length of heat shrink material (not shown) to decrease in size and to reflow the first substrate layer 16. In one embodiment, suitable heat shrink materials include FEP (fluorinated ethylene polypropylene), however, it is noted that other materials possessing similar characteristics would also work, thus the invention is not considered to be so limited. Due to variables such as the pitch of the conductive winding 20 and the thickness of the first, second and third substrate layers 16, 22, 26 it is difficult to characterize the heat treatment necessary to cause the first, second and third substrate layers 16, 22, 26 to reflow. In one embodiment, a vertical reflow system is used (not shown), which is well known to those skilled in the art. A vertical reflow system comprises a cylindrical chamber which is provided with a heat source through which the lead body is sequentially passed. It has been found that the first, second and third substrate layer 16, 22, 26 successfully reflow at a temperature of 450 degrees C., plus or minus 25 degrees C. when passed through a vertical reflow system at a speed of 0.1 to 0.3 centimeters per second. Following reflowing of the first substrate layer 16 the first length of heat shrink material (not shown) is removed and discarded at step 60.

FIG. 3 illustrates step 62 and placement of a conductive coil layer 20 over the outer surface of the first substrate layer 16. The conductive coil layer 20 in one embodiment is MP35N drawn fused tubing sold under the name DFI® but could also be any non-ferromagnetic material having sufficient conductivity to deliver electrical energy through the lead body 100 while maintaining MRI compatibility. The MP35N drawn fused tubing is an insulated conductor which could be insulated by such bio-compatible materials such as Teflon®, polyimide, urethanes or other materials. The conductive coil layer 20 may be initially secured in place using a variety of methods (e.g., crimping, swaging, heat shrink, others)(not shown). It is understood that the winding pattern for the conductive coil layer 20 shown herein is for purposes of illustration only and therefore does not limit the scope of the invention. As an example, the winding pattern as illustrated is monofilar, however, the invention is also compatible with multifilar applications. It is also understood that while a single conductive coil layer is shown in the drawings, this is for purposes of illustration only and therefore additional embodiments utilizing multiple conductive coil layers are also compatible with the method of this invention and therefore within its scope.

In one embodiment the second set of blockers 18 comprises a heat shrink material, where at step 64, the heat shrink material is placed over the coil between the second set of blockers 18 and serves to prevent the migration of the subsequent (i.e., second 22 and third 26) substrate layers. In one embodiment, suitable heat shrink materials include PET (polyethylene terephthalate) heat shrink material, however, it is noted that other materials possessing similar characteristics would also work, thus the invention is not considered to be so limited. Placement of the second set of blockers 18 is followed by the application of heat to cause the heat shrink material to shrink in size.

FIG. 4 shows the application at step 66 of a second substrate layer 22 over the uncompleted lead body. In one embodiment the second substrate layer 22 comprises an 80 A polyurethane material which is a softer material than 55 D polyurethane and functions as a dampener or shock absorber. Additionally, the second substrate layer 22 serves to precisely bind the winding layer 20 to the first substrate layer 16 thus ensuring the accuracy of the intended diameter and pitch of the conductive coil layer 20 which maintains the electrical performance characteristics necessary for MRI compatibility. The second substrate layer 22 is applied to the lead body as a tube which is slid over the tapered end 10a of the mandrel 10 and uncompleted lead body.

FIG. 5 shows the lead body following reflowing of the second substrate 22. Reflowing is accomplished at step 68 by sliding a second length of heat shrink material (not shown) over the second substrate 22 which is then at step 70 exposed to a sufficient amount of heat for a period of time sufficient to cause the heat shrink material (not shown) to decrease in size and to reflow the second substrate layer 22. In one embodiment, suitable heat shrink materials include an FEP (fluorinated ethylene polypropylene) heat shrink material, however, it is noted that other materials possessing similar characteristics would also work, thus the invention is not considered to be so limited. The pressure exerted on the second substrate layer 22 by the decreasing size of the heat shrink material (not shown), in combination with the exposure to heat energy causes the second substrate material 22 to reflow, resulting in the second substrate layer 22 being uniformly molded around the uncompleted lead body, resulting in the conductive winding 20 being permanently secured in place. Reflowing of the second substrate layer 22 also results in the second substrate layer 22 fusing with the first substrate layer 16, while still maintaining separate layers. Following reflowing of the second substrate layer 22 the heat shrink material (not shown) is removed and discarded at step 72.

As shown in FIG. 6, a third substrate layer 26 is applied at step 76 by sliding a tube over the lead body. In one embodiment the third substrate layer 26 comprises a 55 D urethane material which is a relatively firm material, which primarily serves to add strength and an additional degree of integrity to the completed lead body 100. Also shown in FIG. 6 is the addition of a third set of blockers 28 which can be heat shrink material placed towards the outer ends (unnumbered) of the uncompleted lead body. It should be noted that in some embodiments, the third set of blockers 28 may not be used, depending on the thicknesses of the substrate layers. Placement of the third set of blockers 28 is followed by the application of heat to cause the heat shrink material to reduce in size, thereby securing the third set of blockers at the desired position on the lead body. When used, the third set of blockers 28 functions to prevent the reflowed third substrate layer 26 from flowing beyond the third set of blockers 28. The third set of blockers 28 can be made of PET (polyethylene terephthalate) heat shrink material, however, it is noted that other materials possessing similar characteristics would also work, thus the invention is not considered to be so limited.

FIG. 7 shows reflowing the third substrate 26 which is accomplished at step 78 by sliding a third length of heat shrink material (not shown) over the third substrate layer 26 which is then at step 80 exposed to a sufficient amount of heat for a period of time sufficient to cause the heat shrink material (not shown) to decrease in size and reflow the third substrate layer 26. In one embodiment, suitable heat shrink materials include an FEP (fluorinated ethylene polypropylene) heat shrink material, however, it is noted that other materials possessing similar characteristics would also work, thus the invention is not considered to be so limited. Following reflowing of the third substrate layer 26 the heat shrink material (not shown) is removed and discarded at step 82. The pressure exerted on the third substrate layer 26 by the decreasing size of the heat shrink material, in combination with the exposure to heat energy causes the third substrate material 26 to reflow, resulting in the third substrate layer 26 being uniformly molded around the lead body. Reflowing of the third substrate layer 26 also results in the third substrate layer 26 fusing with the second substrate layer 22, while still maintaining separate layers.

FIG. 8 shows the lead body 100 following removal of the mandrel 10. It is noted that a lumen 30 is formed where the mandrel 10 had previously been in place. Removal of the mandrel 10 at step 84 first requires loosening of the first, second and third sets of blockers 14, 18, 28, which frees the mandrel 10 from the lead body 100, allowing the mandrel 10 at step 86 to be withdrawn from the lead body 100 without damaging the lead body 100. The function of the first, second and third sets of blockers 14, 18, 28 is to ensure that the first, second and third reflowed substrate layers 16, 22, 26 end at the same point. In one embodiment they would be perfectly aligned, but perfect alignment is not absolutely required.

Following removal of the lead body 100 from the mandrel 10, the lead body 100 is trimmed (not shown) at step 88 to expose the conductive coil layer 20, allowing later attached electrodes and connectors to be in electrical communication with various devices.

Figure 9A:
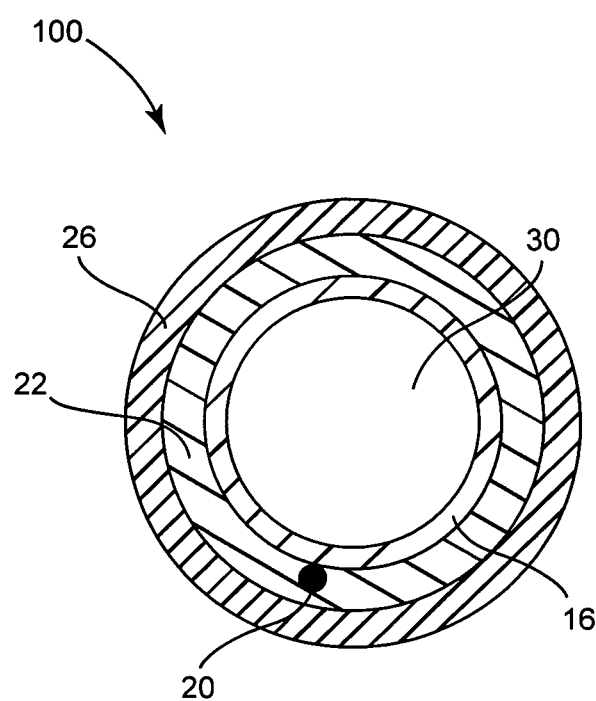
FIG. 9A is a lateral cross section of the lead body taken through the lines 9A-9A of FIG. 9.

FIG. 9A is a lateral cross section taken through the lines 9A-9A of the completed lead body 100 (FIG. 9) and shows the various layers built up during the manufacturing process and the lumen 30.

Figure 10:
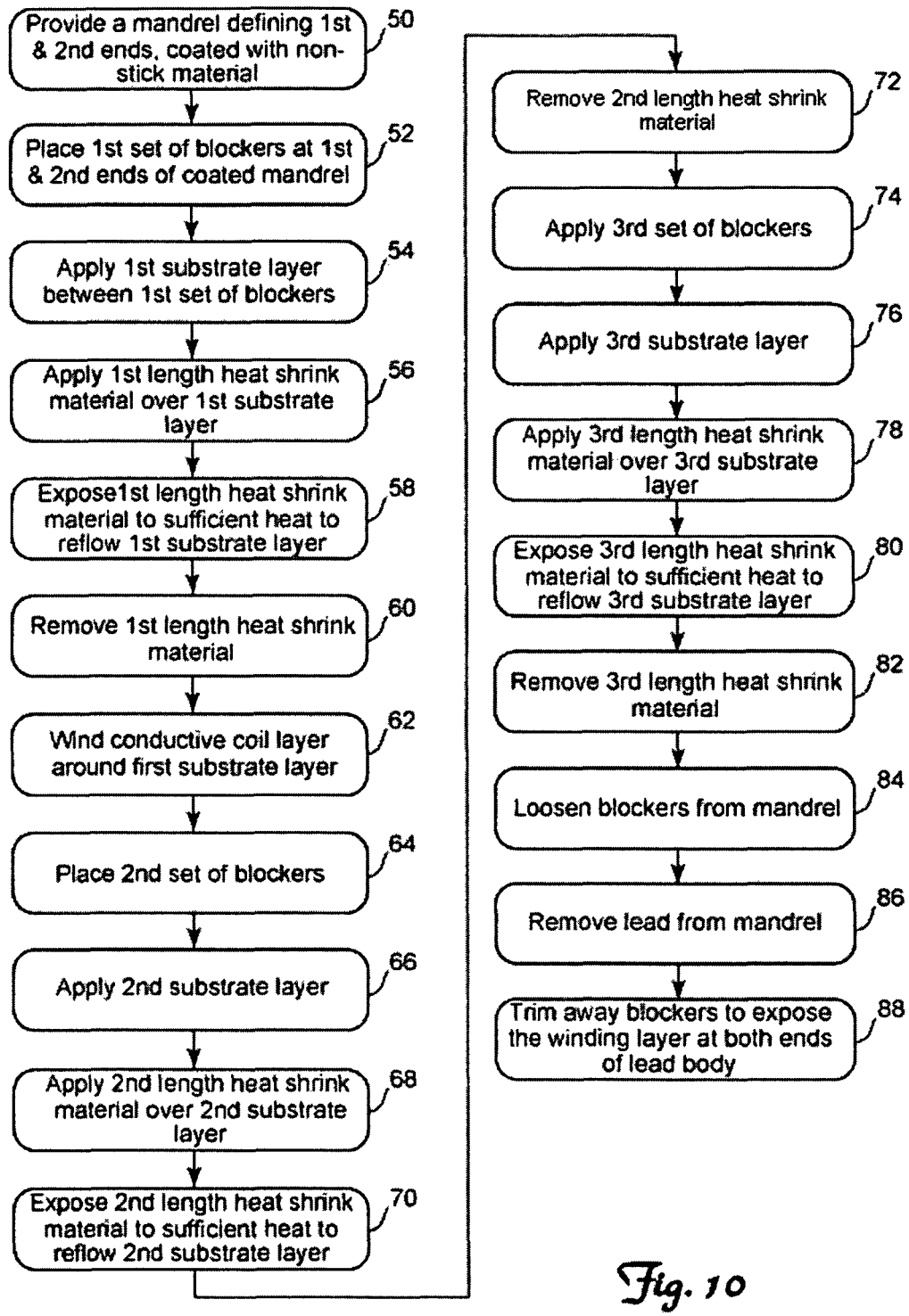
FIG. 10 is a flow chart illustrating the steps of the method of the invention.

FIG. 10 is a flow chart illustrating the various steps of the manufacturing process, including reflowing of the first, second and third substrate layers 16, 22, 26.

What is claimed is:

1. A method of manufacturing an implantable electrical lead body that is MRI compatible for the purpose of diagnostic quality imaging, comprising the steps of:
    a. providing a mandrel defining a first end, a second end and an outer diameter;
    b. applying a first substrate layer over the mandrel;
    c. reflowing the first substrate layer to conform closely to the mandrel;
    d. winding at least one conductive coil layer around the outer surface of the first substrate layer, wherein the conductive coil layer as a helix pitch and diameter;
    e. securing the conductive coil layer to the mandrel at least at the first end and the second end;
    f. applying a second substrate layer over the first substrate layer and the conductive coil layer;
    g. reflowing the second substrate layer to fuse with the first substrate layer and encapsulate the conductive coil layer, permanently securing the conductive coil layer to the lead body and preserving the helix pitch and diameter;
    h. applying a third substrate layer over the second substrate layer;
    i. reflowing the third substrate layer to fuse with the second substrate layer;
    j. removing the lead body from the mandrel; and
    k. trimming the lead body to expose the conductive coil layer, allowing the lead body to be capable of electrical communication.

2. The method of claim 1 wherein the first substrate layer and the third substrate layers have a similar flexibility.

3. The method of claim 1 wherein the second substrate layer is a softer material than the first substrate layer and the third substrate layer.

4. The method of claim 3 wherein the first substrate layer and third substrate layer are made of a 55D polyurethane material.

5. The method of claim 3 wherein the second substrate layer is made from an 80A polyurethane material.

6. The method of claim 1 wherein reflowing the first, second and third substrate layers progressively uses first, second and third lengths of heat shrink material over the first, second and third substrate layers followed by the application of sufficient amounts of heat for periods of time sufficient to cause the first, second and third lengths of heat shrink material to decrease in size and to reflow the respective first, second and third substrate layers.

7. The method of claim 1 wherein reflowing the first substrate layer uses a first length of heat shrink material over the mandrel followed by the application of a sufficient amount of heat for a period of time sufficient to cause the first length of heat shrink material to decrease in size and reflow the first substrate layer, reflowing the second substrate layer uses a second length of heat shrink material over the mandrel followed by the application of a sufficient amount of heat for a period of time sufficient to cause the second length heat shrink material to decrease in size and reflow the second substrate layer and reflowing the third substrate layer uses a third length of heat shrink material over the mandrel followed by the application of a sufficient amount of heat for a period of time sufficient to cause the third length of heat shrink material to decrease in size and reflow the third substrate layer.

8. The method of claim 1 wherein the first end of the mandrel is tapered.

9. A method of manufacturing an implantable electrical lead body that is MRI compatible for the purpose of diagnostic quality imaging, comprising the steps of:
    a. providing a mandrel defining a first end and a second end and an outer dimension substantially conforming to a desired inner dimension of a lumen defined by the lead body, the mandrel coated with a non-stick material;
    b. placing a first set of blockers at the first and second end of the mandrel, the first set of blockers serving to prevent the migration of subsequently applied layers during the method;
    c. applying a first substrate layer between the first set of blockers;
    d. applying a first length of heat shrink material over the first substrate;
    e. exposing the first length of heat shrink material to a sufficient amount of heat for a sufficient length of time to cause the first substrate layer to reflow, resulting in the first substrate layer conforming to the coated mandrel;
    f. removing the first length of heat shrink material;
    g. winding at least one conductive coil layer over the outer surface of the first substrate layer;
    h. securing the conductive coil layer to the mandrel;
    i. placing a second set of blockers at the first and second end of the lead body;
    j. applying a second substrate layer between the second set of blockers;
    k. applying a second length of heat shrink material over the second substrate;
    l. exposing the second length of heat shrink material to a sufficient amount of heat for a sufficient length of time to cause the second substrate layer to reflow, resulting in the second substrate layer encapsulating the conducting coil layer and fusing with the first substrate layer;
    m. removing the second length of heat shrink material;
    n. applying a third substrate material over the uncompleted lead body;
    o. applying a third length of heat shrink material over the third substrate;
    p. exposing the third length of heat shrink material to a sufficient amount of heat for a sufficient length of time to cause the third substrate layer to reflow and bond with the second substrate layer;
    q. removing the third length of heat shrink material;
    r. loosening the blockers from the mandrel;
    s. removing the lead body from the mandrel; and t. removing the blockers to expose the conductive coil layer, allowing the lead body to be capable of electrical communication.

10. The method of claim 9 wherein the first substrate layer and the third substrate layers have a similar flexibility.

11. The method of claim 9 wherein the second substrate layer is a softer material than the first substrate layer and the third substrate layer.

12. The method of claim 11 wherein the first substrate layer and third substrate layer are a 55D polyurethane material.

13. The method of claim 11 wherein the second substrate layer is an 80A polyurethane material.

14. The method of claim 9 wherein the reflowed first substrate layer has a substantially similar outer dimension as the first set of blockers.

15. The method of claim 9 wherein the reflowed second substrate layer has a substantially similar outer dimension as the second set of blockers.

16. The method of claim 9 wherein a third set of blockers is placed on the lead body following winding of the conductive coil layer and before application of the third substrate layer.

17. The method of claim 9 wherein the first end of the mandrel is tapered.

18. A method for fabricating an electrical lead for an implantable electronic medical device, said method comprising:
   a. placing a first tube of a polymer over a mandrel;
   b. placing a first heat shrinkable tubing over the mandrel and the first tube;
   c. applying heat to shrink the first heat shrinkable tubing around the first tube and to reflow the first tube to conform to the mandrel;
   d. removing the first heat shrinkable tubing from the first tube;
   e. winding an electrical conductor in a longitudinal spiral around the first tube, thereby forming a conductive coil layer;
   f. placing a second tube of a polymer over the mandrel, the first tube, and the conductive coil layer;
   g. placing a second heat shrinkable tubing over the mandrel, the first tube, the conductive coil layer, and the second tube; and
   h. applying heat to shrink the second heat shrinkable tubing around the second tube and reflow the second tube to fuse with the first tube and encapsulate the conductive coil layer.

19. The method as recited in claim 18 further comprising:
   i. removing the second heat shrinkable tubing from around the second tube;
   j. placing a third tube of a polymer over the mandrel, the first tube, the conductive coil layer, and the second tube;
   k. placing a third heat shrinkable tubing over the mandrel, the first tube, the conductive coil layer, the second tube and the third tube; and
   l. applying heat to reflow the third tube and shrink the third heat shrinkable tubing around the third tube.

20. The method as recited in claim 19 further comprising removing the third heat shrinkable tubing from around the third tube.

21. The method of claim 18 wherein each step of placing a first tube and placing a second tube results in the first and second tube extending proximate to first and second ends of the implantable electrical lead.

22. The method of claim 1 wherein each step of applying a first substrate layer, applying a second substrate layer, and applying a third substrate layer results in the respective substrate layer extending proximate to first and second ends of the implantable electrical lead.

23. The method of claim 9 wherein each step of applying a first substrate layer, applying a second substrate layer, and applying a third substrate layer results in the respective substrate layer extending proximate to first and second ends of the implantable electrical lead.

* * * * *